United States Patent [19]

Bru-Magniez et al.

[11] Patent Number: 5,192,781
[45] Date of Patent: Mar. 9, 1993

[54] THIAZOLE DERIVATIVES WHICH ARE ANGIOTENSIN II RECEPTOR ANTAGONISTS, THEIR METHODS OF PREPARATION AND PHARMACEUTICAL COMPOSITIONS IN WHICH THEY ARE PRESENT

[75] Inventors: Nicole Bru-Magniez, Paris; Michéle Launay, Rueil-Malmaison; Jean-Marie Teulon, La Celle Saint Cloud, all of France

[73] Assignee: Laboratoires UPSA, Agen, France

[21] Appl. No.: 728,393

[22] Filed: Jul. 11, 1991

[30] Foreign Application Priority Data

May 31, 1991 [FR] France ................... 91 06595

[51] Int. Cl.$^5$ ............. A61K 31/425; C07D 277/30
[52] U.S. Cl. ........................ 514/365; 514/369; 514/370; 514/371; 548/187; 548/193; 548/194; 548/195; 548/198; 548/202; 548/203; 548/204; 548/205
[58] Field of Search ............ 548/193, 187, 194, 195, 548/198, 202, 203, 204, 205; 514/370, 369, 365, 371

[56] References Cited

U.S. PATENT DOCUMENTS 5,071,864 12/1991 Rendenbech-Mueller ......... 514/370
5,073,562 12/1991 Djuric ........................... 514/365

FOREIGN PATENT DOCUMENTS 0283390 9/1988 European Pat. Off. .
0401030 12/1990 European Pat. Off. .
412404 2/1991 European Pat. Off. ............ 548/193

OTHER PUBLICATIONS

Chemical Abstracts, vol. 105, No. 23, Dec. 8, 1986, Columbus, Ohio, US; Abstract No. 208866F.

Primary Examiner—Robert Gerstl
Attorney, Agent, or Firm—Armstrong, Westerman, Hattori, McLeland & Naughton

[57] ABSTRACT

The present invention relates to the derivatives of formula (I):

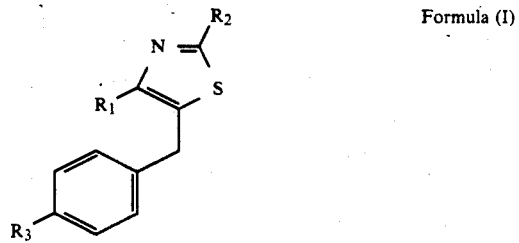

Formula (I)

and their addition salts, and to their use in therapeutics, especially for the treatment of cardiovascular diseases and in particular for the treatment of hypertension and cardiac insufficiency.

8 Claims, No Drawings

THIAZOLE DERIVATIVES WHICH ARE ANGIOTENSIN II RECEPTOR ANTAGONISTS, THEIR METHODS OF PREPARATION AND PHARMACEUTICAL COMPOSITIONS IN WHICH THEY ARE PRESENT

The present invention relates, by way of novel products, to the thiazole derivatives of general formula (I) below and their addition salts, in particular the pharmaceutically acceptable addition salts.

The compounds in question have a very valuable pharmacological profile insofar as they possess antagonistic properties towards angiotensin II receptors. They are therefore especially indicated for the treatment of cardiovascular diseases and in particular for the treatment of hypertension and the treatment of cardiac insufficiency.

The present invention further relates to the method of preparing said products and to their applications in therapeutics.

These thiazole derivatives have general formula (I):

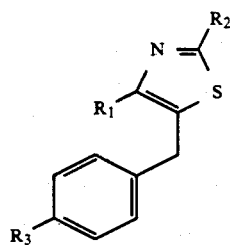

Formula (I)

in which:

$R_1$ is a lower alkyl radical having 1 to 6 carbon atoms or a $C_3$-$C_7$ cycloalkyl radical;

$R_2$ is the hydrogen atom, a halogen atom, a lower alkyl radical having 1 to 6 carbon atoms, a lower halogenoalkyl radical having 1 to 6 carbon atoms, a $C_3$-$C_7$ cycloalkyl radical or an aromatic or heteroaromatic ring; $R_2$ can also be a group $X-(CH_2)_n-CN$, $X-(CH_2)_n-COOR_4$, $X-(CH_2)_n-OR_4$, $X-(CH_2)_n-SR_4$, $X-(CH_2)_n-NR'R''$, $X-(CH_2)_n-CO-NR'R''$ $NR'R''$ or $X-(CH_2)_n-NHCOR_5$; in these groups, X is a bond, a sulfur atom or a group NH, n is an integer from 0 to 5, $R_4$ is a hydrogen atom, a lower alkyl radical having 1 to 6 carbon atoms, a lower halogenoalkyl radical having 1 to 6 carbon atoms or a $C_3$-$C_7$ cycloalkyl radical, $R_5$ is defined in the same way as $R_4$ except that it can also be an aromatic or heteroaromatic ring or a methanebiphenyl, and $R'$ and $R''$ are independently a hydrogen atom, a lower alkyl radical having 1 to 6 carbon atoms or a $C_3$-$C_7$ cycloalkyl radical or they can form, together with the nitrogen atom to which they are attached, a heterocycle such as pyrrolidine, piperidine, morpholine, thiomorpholine or a piperazine, it being possible for the latter to be substituted on the second nitrogen atom by a lower alkyl having 1 to 6 carbon atoms or an aromatic or heteroaromatic ring; and $R_3$ is a nitro or amino group or one of the following groups:

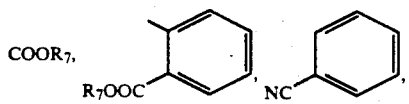

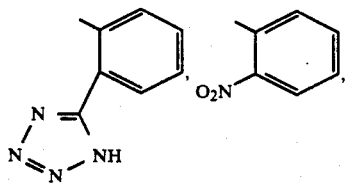

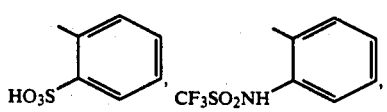

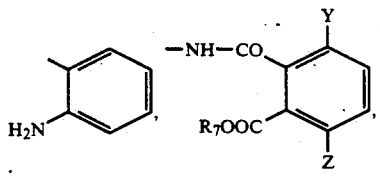

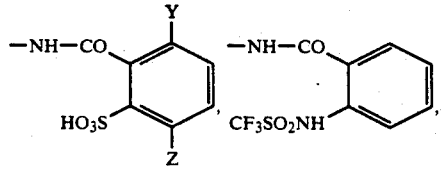

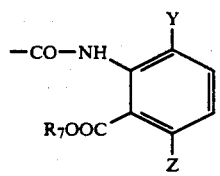

in which $R_7$ is a hydrogen atom, a lower alkyl radical having 1 to 6 carbon atoms or else a benzyl radical and Y and Z are independently a hydrogen atom, a halogen atom, a lower alkyl radical having 1 to 6 carbon atoms, an O-lower alkyl radical or a trifluoromethyl.

These derivatives can take the form of addition salts, in particular pharmaceutically acceptable addition salts.

In the description and the claims, lower alkyl is understood as meaning a linear or branched hydrocarbon chain having from 1 to 6 carbon atoms. A lower alkyl is, for example, a methyl, ethyl, propyl, isopropyl, butyl, isobutyl, tert-butyl, pentyl, isopentyl, hexyl or isohexyl radical.

$C_3$-$C_7$ cycloalkyl radical is understood as meaning a saturated cyclic radical, preferably a cyclopropane, cyclobutane, cyclopentane, cyclohexane or cycloheptane radical.

Halogen is understood as meaning a chlorine, bromine, iodine or fluorine atom.

Lower halogenoalkyl radical having 1 to 6 carbon atoms is understood as meaning an alkyl radical in which 1 to 7 hydrogen atoms have been substituted by 1 to 7 halogen atoms. A lower halogenoalkyl radical is, for example, a trifluoromethyl radical, a 2,2,2-trifluoroethyl radical, a pentafluoroethyl radical, a 2,2-difluoro- 3,3,3-trifluoropropyl radical or a heptafluoropropyl radical.

Aromatic ring is understood as meaning a phenyl ring and heteroaromatic ring is understood as meaning an aromatic ring having 5 to 7 atoms and containing at least one heteroatom such as nitrogen, oxygen or sulfur, it being possible for the phenyl or heteroaromatic ring to be unsubstituted or substituted by a lower alkyl group, a halogen, a lower halogenoalkyl group, an O-lower alkyl radical or an S-lower alkyl radical.

According to one embodiment, $R_1$ is an n-propyl group.

According to one embodiment, $R_2$ is a methyl group.

According to another embodiment, $R_2$ is a methoxymethylene group.

According to one embodiment, $R_3$ is a 2-sulfoxybenzoylamino group.

The particularly preferred compounds of the invention are those selected from the products of the formulae

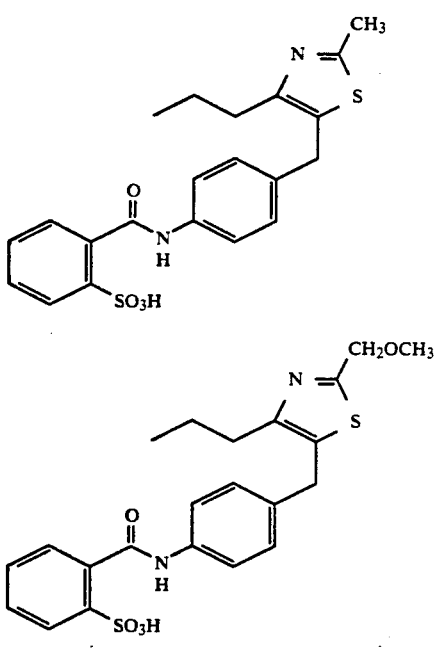

According to the invention, the compounds of formula (I) may be synthesized by the following reaction sequence:

In a first stage, vinyl ketones of formula (II):

$R_1$—CO—CH=CH$_2$  Formula (II) 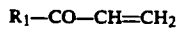

in which $R_2$ is as defined above, will be synthesized.

These vinyl ketones are commercially available, such as vinyl methyl ketone, or can be prepared by known methods described in the literature: R. B. WOODWARD, F. SONDHEIMER, D. TAUB, K. HEUSLER and W. M. McLAMORE: J. Am. Chem. Soc. 1952, 74, 4223, and A. ARCHER, W. B. DICKINSON and M. J. UNSER: J. Org. Chem. 1957, 22, 92, i.e. a Friedel-Crafts reaction of an acid chloride of the formula $R_2COCl$, in which $R_1$ is as defined above, with ethylene in the presence of aluminum chloride will give the chloroketones of the formula $R_1$—CO—CH$_2$CH$_2$—Cl, in which $R_1$ is as defined above, which will be dehydrochlorinated by distillation in the presence of sodium benzoate to give the vinyl ketones of formula (II).

The addition of a diazo derivative of formula (III):

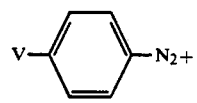

Formula (III)

on to the vinyl ketones of formula (II) in the presence of cupric chloride, under the conditions described in German patent 1,128,429 (1962), will give the chloroketones of formula (IV):

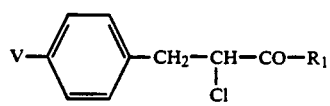

Formula (IV)

in which $R_2$ is as defined above.

The diazo derivatives of formula (III) are obtained by the conventional methods of diazotizing the anilines of formula (V):

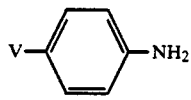

Formula (V)

with NaNO$_2$ in the presence of hydrochloric acid.

In formulae (III), (IV) and (V), V can be a nitro group, in which case commercially available paranitroaniline will be used.

V can be a group COOR$_7$, R$_7$ being as defined above, in which case commercially available p-aminobenzoic acid or, preferably, one of its esters will be used.

V can be a group

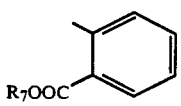

R$_7$ being as defined above, in which case the anilines required for this preparation will be synthesized by the hydrogenation, in the presence of Raney nickel at atmospheric pressure, of 4'-nitrobiphenyl-2-carboxylic acid or one of its esters, synthesized by the method described by DANNLEY R. L. and STERNFELD M., J. Am. Chem. Soc. 1954, 76, 4543.

V can be a group

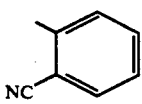

in which case 4'-nitrobiphenyl-2-carboxylic acid prepared according to the previous reference will be treated with thionyl chloride, and the resulting acid chloride will react with ammonia to give 2-(4-nitrophenyl)benzamide. This will be dehydrated by the conventional methods known to those skilled in the art, for example treatment with phosphorus oxychloride in dimethylformamide or with thionyl chloride. Hydrogenation of the resulting 2-(4-nitrophenyl)benzonitrile in the presence of Raney nickel at atmospheric pressure will give the anilines of formula (V) in which V is

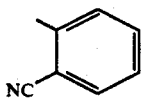

V can be a group

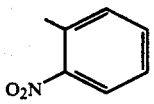

in which case treatment of 2-nitrobiphenyl with acetyl chloride, under the conditions of a Friedel-Crafts reaction, in the presence of aluminum chloride in methylene chloride will give 4-(2-nitrophenyl)acetophenone, which will be converted to the oxime by heating with hydroxylamine in an alcohol, this oxime will be converted to 4-(2-nitrophenyl)acetanilide, under the conditions of a Beckmann rearrangement, in an acid medium and hydrolysis of the amide group will give the anilines of formula (V) in which V is

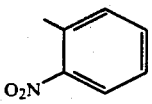

Reaction of derivatives of formula (VI):

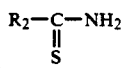  Formula (VI)

in which $R_2$ is as defined above, with the chloroketones of formula (IV), by heating at a temperature of between 20° and 90° C. without a solvent or in an alcohol, will give the derivatives of formula (VII):

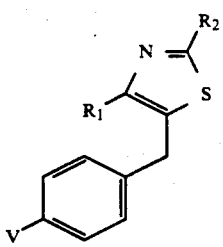  Formula (VII)

in which $R_1$, $R_2$ and V are as defined above.

The derivatives of formula (VI) may be commercially available, as in the case of thiourea, an ester or a salt of aminocarbodithioic acid, thioacetamide or cyanothioacetamide, for example, or can be prepared by conventional methods known to those skilled in the art by reacting $H_2S$ with the corresponding nitrile derivatives in the presence of a base such as pyridine or triethylamine, or by reacting $P_2S_5$ or Lawesson's reagent (2,4-bis(4-methoxyphenyl)-1,3-dithia-2,4-diphosphetane 2,4-disulfide) with the corresponding amide derivatives. These reactions can be found in the following references:

S. EGGERS; V. V. KANE; G. LOWE; J. Chem. Soc. 1965, 1262,

W. WOLFGANG; K. D. BODE; Justus Liebigs Ann. Chem. 1966, 698, 131,

M. ERNE; H. ERLENMEYER; Helv. Chim. Acta 1948, 652,

A. BONZOM; J. METZGER; Bull. Soc. Chim. Fr. 1963, 11, 2582,

O. WALLACH; Ber. 1899, 32, 1874,

N. SCHENK; F. V. GRAEWENITZ; Z. Physiol. Chem. 1924, 141, 138,

A. WEDDIGE; J. Pr. Chem. 1874, 9, 133,

W. R. BOON; J. Chem. Soc. 1945, 601, and

J. F. OLIN; T. B. JOHNSON; Rec. Trav. Chem. 1931, 50, 72.

The derivatives of formula (VII) in which V is a nitro group may be subjected to catalytic hydrogenation, for example in the presence of Raney nickel in an alcohol, at atmospheric pressure and at room temperature, to give the compounds of formula (I) in which $R_3$ is an amino group.

Reaction of an appropriately substituted phthalic anhydride with these derivatives will give the compounds of general formula (I) in which $R_3$ is the group

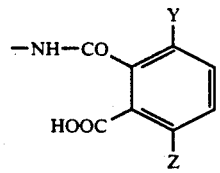

in which Y and Z are as defined above, it then being possible for the acid obtained to be esterified to give the group

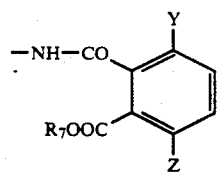

in which Y, Z and $R_7$ are as defined above.

Likewise, reaction of an appropriately substituted cyclic anhydride of orthosulfobenzoic acid with these amine compounds will give the compounds of general formula (I) in which $R_3$ is the group

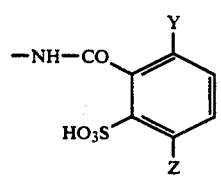

in which Y and Z are as defined above.

Likewise, reaction of N-(trifluoromethylsulfonyl)anthranilic acid chloride, whose preparation can be found in the following references:

CA 96(15) : 103651 Z, and

CA 97(7) : 55500 W, with these amine compounds will give the compounds of general formula (I) in which $R_3$ is the group

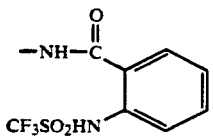

The derivatives of formula (VII) in which V is a group COOR$_7$ may be hydrolyzed in an acidic or basic medium, or else hydrogenated in the case where R$_7$ is a benzyl so as not to affect the other ester groups which may be present, to give the compounds of formula (I) in which R$_3$ is a group COOH.

After these acids have been converted to the acid chloride with thionyl chloride or to a mixed anhydride with ethyl chloroformate in the presence of triethylamine, reaction with anthranilic acid derivatives of the formula

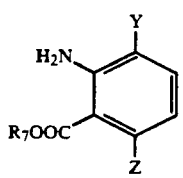

in which Y, Z and R$_7$ are as defined above, may give the compounds of general formula (I) in which R$_3$ is the group

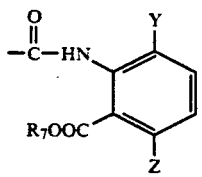

The derivatives of formula (VII) in which V is a group

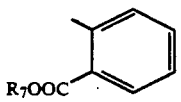

will likewise be hydrolyzed, or hydrogenated in the presence of a catalyst, such as palladium-on-charcoal, in the case where R$_7$ is a benzyl, to give the compounds of formula (I) in which R$_3$ is a group

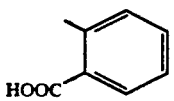

The derivatives of formula (VII) in which V is a group

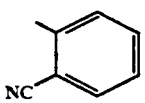

may react with one equivalent of sodium nitride in a solvent such as dimethylformamide, in the presence of an ammonium salt such as ammonium chloride, or else with a trialkyltin nitride under reflux in toluene and then with gaseous hydrogen chloride in tetrahydrofuran, to give the compounds of general formula (I) in which R$_3$ is a group

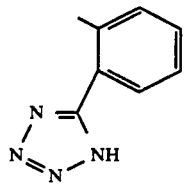

The derivatives of formula (VII) in which V is a group

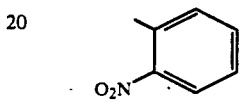

may be subjected to catalytic hydrogenation, for example in the presence of Raney nickel in an alcohol, at atmospheric pressure or under pressure and at room temperature, to give compounds of formula (I) in which R$_3$ is a group

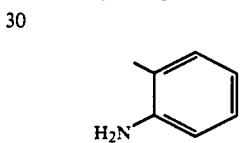

Reaction of trifluoromethanesulfonyl chloride or trifluoromethanesulfonic anhydride with these compounds in a solvent such as chloroform or in an aromatic solvent such as toluene, in the presence of a base such as triethylamine or pyridine, or in pyridine, will give the compounds of general formula (I) in which R$_3$ is the group

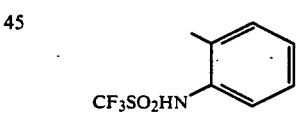

Diazotization of these amine compounds followed by treatment of the diazo compound with SO$_2$ in a dilute sulfuric acid medium, in the presence of copper, gives the sulfinic acid derivatives, which will be oxidized with hydrogen peroxide or potassium permanganate according to the following reference:
GATTERMANN L., Ber. 1899, 1136,
to give the derivatives of formula (I) in which R$_3$ is the group

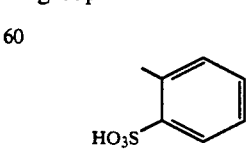

It is possible to obtain addition salts of some of the compounds of formula (I), especially pharmaceutically acceptable addition salts. In particular, when R$_2$ or R$_3$ contains an acid group, there may be mentioned the salts of sodium, potassium, calcium, an amine such as dicyclohexylamine or an amino acid such as lysine. When $R_2$ or $R_3$ contains an amine group, there may be mentioned the salts of a mineral or organic acid, such as the hydrochloride, methanesulfonate, acetate, maleate, succinate, fumarate, sulfate, lactate or citrate, for example.

The novel compounds according to the invention possess remarkable properties as angiotension II receptor antagonists and can be used in therapeutics for the treatment of cardiovascular diseases and in particular for the treatment of hypertension and cardiac insufficiency.

Thus the invention covers the pharmaceutical compositions which contain, as the active principle, the drugs consisting of a pharmaceutically effective amount of at least one compound of formula (I) as defined above, or one of its pharmaceutically acceptable addition salts if appropriate.

These compositions can be administered by the buccal, rectal, parenteral, transdermal or ocular route.

These compositions can be solid or liquid and can take the pharmaceutical forms commonly used in human medicine, such as, for example, simple or coated tablets, gelatin capsules, granules, suppositories, injectable preparations, transdermal systems and eye lotions; they are prepared by the customary methods. In said compositions, the active principle, consisting of a pharmaceutically effective amount of at least one compound of formula (I) as defined above, or one of its pharmaceutically acceptable addition salts, can be incorporated with excipients normally employed in these pharmaceutical compositions, such as talc, gum arabic, lactose, starch, magnesium stearate, polyvidone, cellulose derivatives, cocoa butter, semisynthetic glycerides, aqueous or non-aqueous vehicles, fats of animal or vegetable origin, glycols, various wetting agents, dispersants or emulsifiers, silicone gels, certain polymers or copolymers, preservatives, flavorings and colors.

The invention also covers a pharmaceutical composition with antagonistic activity towards angiotensin II receptors, which makes it possible especially to favorably treat cardiovascular diseases, in particular hypertension and cardiac insufficiency, said composition comprising a pharmaceutically effective amount of at least one compound of formula (I) mentioned above, or one of its pharmaceutically acceptable addition salts, which may be incorporated in a pharmaceutically acceptable excipient, vehicle or carrier.

The dosage varies especially according to the route of administration, the complaint treated and the subject in question.

For example, for an adult with an average weight of 60 to 70 kg, it can vary between 1 and 400 mg of active principle, administered orally in one or more daily doses, or from 0.01 to 50 mg, administered parenterally in one or more daily doses.

The invention also covers a method of preparing a pharmaceutical composition, which comprises incorporating a pharmaceutically effective amount of at least one compound of formula (I) as defined above, or one of its pharmaceutically acceptable addition salts, into a pharmaceutically acceptable excipient, vehicle or carrier. According to a particular characteristic, this pharmaceutical composition is formulated as gelatin capsules or tablets containing from 1 to 400 mg of active principle, or as injectable preparations containing from 0.01 to 50 mg of active principle.

The invention also covers a method of therapeutic treatment for mammals, which comprises administering to this mammal a therapeutically effective amount of at least one compound of formula (I) as defined above, or one of its pharmaceutically acceptable addition salts.

In animal therapeutics, the daily dose which can be used should normally be between 1 and 100 mg per kg.

Further characteristics and advantages of the invention will be understood more clearly from the following description of some Preparatory Examples, which in no way imply a limitation but are given by way of illustration.

EXAMPLE 1

3-Chloro-4-(4-nitrophenyl)butan-2-one

Formula IV: $R_1=CH_3$, $V=NO_2$ 27.6 g of 4-nitroaniline are dissolved in 180 ml of 20% hydrochloric acid. The solution is cooled to 0°–5° C. and a solution of 12.7 g of sodium nitrite in 30 ml of water is then added slowly, with cooling. The pH is then raised to 3 with a 25% solution of sodium hydroxide, the temperature being kept at 5°–10° C. A solution of 4.7 g of $CuCl_2$ in 25 ml of water is added, followed by a solution of 17.3 ml of but-3-en-2-one in 180 ml of acetone. The reaction mixture is allowed to return to room temperature. After one night, it is decanted and the organic phase is concentrated. The residue is taken up with water and extracted with chloroform. After drying, the filtrate is concentrated to give a red oil, which is purified by chromatography on a silica column (eluent: 50/50 chloroform/petroleum ether) to give 15.4 g of 3-Chloro-4-(4-nitrophenyl)-butan-2-one in the form of an orange solid melting at 86° C.

EXAMPLE 2

2,4-Dimethyl-5-(4-nitrobenzyl)thiazole

Formula VII: $R_1=CH_3$, $R_2=CH_3$, $V=NO_2$ 4.7 g of 3-chloro-4-(4-nitrophenyl)butan-2-one and 2.4 g of thioacetamide are dissolved in 60 ml of ethanol and refluxed for 12 hours. The reaction medium is concentrated, the residue is taken up in water and the solution is rendered basic with sodium carbonate and extracted with chloroform. After concentration of the organic phase, the solid obtained is taken up in hot pentane to give 3.5 g of 2,4-dimethyl-5-(4-nitrobenzyl)-thiazole in the form of yellow crystals melting at 66° C.

EXAMPLE 3

2,4-Dimethyl-5-(4-aminobenzyl)thiazole

Formula I: $R_1=CH_3$, $R_2=CH_3$, $R_3=NH_2$ 3.5 g of 2,4-dimethyl-5-(4-nitrobenzyl)thiazole in 50 ml of methanol are hydrogenated at normal pressure and room temperature in the presence of Raney nickel. After filtration of the catalyst and concentration of the reaction medium, 3 g of 2,4-dimethyl-5-(4-aminobenzyl)thiazole are obtained in the form of a brown solid melting at 120° C.

EXAMPLE 4

2-[4-((2,4-Dimethylthiazol-5-yl)methyl)-phenylaminocarbonyl]benzoic acid

Formula I: $R_1=CH_3$, $R_2=CH_3$,

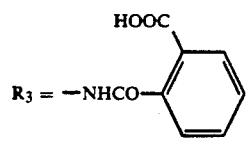

$R_3 = -NHCO-$ 3 g of 2,4-dimethyl-5-(4-aminobenzyl)thiazole are dissolved in 75 ml of acetonitrile, and 2 g of phthalic anhydride are added in portions. The medium is stirred for 6 hours at room temperature and the precipitate is then filtered off and washed with ethyl acetate to give 3.3 g of 2-[4-((2,4-dimethylthiazol-5-yl)methyl)-phenylaminocarbonyl]benzoic acid in the form of crystals melting at 182° C.

EXAMPLE 5

Ethyl (4-methyl-5-(4-nitrobenzyl)thiazol-2-yl)aminoacetate

Formula VII: $R_1=CH_3$, $R_2=NHCH_2COOEt$, $V=NO_2$ 7.6 g of 3-chloro-4-(4-nitrophenyl)butan-2-one and 4.5 g of N-carboxymethylthiourea ($NH_2CSNHCH_2COOH$) are dissolved in 100 ml of ethanol and refluxed for 12 hours. The reaction medium is concentrated and the residue is recrystallized from isopropanol to give 9.5 g of ethyl (4-methyl-5-(4-nitrobenzyl)thiazol-2-yl)aminoacetate.

EXAMPLE 6

Ethyl (4-methyl-5-(4-aminobenzyl)thiazol-2-yl)aminoacetate

Formula I: $R=CH_3$, $R_2=NHCH_2COOEt$, $R_3=NH_2$ 9.2 g of ethyl (4-methyl-5-(4-nitrobenzyl)thiazol-2-yl)aminoacetate in 500 ml of an ethanol/methoxyethanol mixture are hydrogenated at normal pressure and room temperature in the presence of Raney nickel. After filtration of the catalyst and concentration of the reaction medium, a brown oil is obtained which is taken up with acidified water, the aqueous phase is extracted with chloroform and then rendered basic and the precipitate obtained is filtered off to give 6.1 g of ethyl (4-methyl-5-(4-aminobenzyl)thiazol-2-yl)aminoacetate in the form of a brown solid melting at 116° C.

EXAMPLE 7

Ethyl (4-methyl-5-(4-(2-carboxybenzoylamino)benzyl)thiazol-2-yl)aminoacetate

Formula I: $R_1=CH_3$, $R_2=NHCH_2COOEt$,

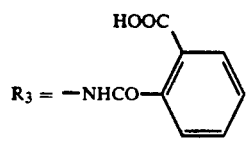

$R_3 = -NHCO-$ 6 of ethyl (4-methyl-5-(4-aminobenzyl)thiazol-2-yl)aminoacetate are dissolved in 150 ml of tetrahydrofuran, and 2.9 g of phthalic anhydride are added in portions. The medium is stirred for 4 hours at room temperature, the insoluble material is then removed and the filtrate is concentrated. The residue is taken up in water rendered basic with sodium bicarbonate and the solution is washed with chloroform and then acidified to give 2.2 g of ethyl (4-methyl-5-(4-(2-carboxybenzoylamino)benzyl)thiazol-2-yl) aminoacetate in the form of crystals melting at 206°-8° C.

EXAMPLE 8

2-Chloro-1-(4-nitrophenyl)hexan-3-one

Formula IV: $R_2=CH_2CH_2CH_3$, $V=NO_2$ 60 g of 4-nitroaniline are dissolved in 485 ml of 20% hydrochloric acid. The solution is cooled to 0°-5° C. and a solution of 26.7 g of sodium nitrite in 65 ml of water is then added slowly, with cooling. The pH is raised to 3 with a 25% solution of sodium hydroxide (300 ml), the temperature being kept at 5°-10° C. A solution of 11.6 g of $CuCl_2$ in 75 ml of water is added, followed by a solution of 44.3 g of hex-1-en-3-one in 390 ml of acetone. The reaction mixture is allowed to return to room temperature, when the evolution of nitrogen and a temperature increase are observed. The reaction mixture is left overnight. It is decanted and the organic phase is concentrated. The residue is taken up with water and extracted with chloroform. After drying, the filtrate is concentrated to give a red oil, which is purified by chromatography on a silica column (eluent: cyclohexane) to give 57.9 g of 2-chloro-1-(4-nitrophenyl)hexan-3-one in the form of an orange oil.

EXAMPLE 9

2-Methyl-4-propyl-5-(4-nitrobenzyl)thiazole

Formula VII: $R_1=CH_2CH_2CH_3$, $R_2=CH_3$, $V=NO_2$

A mixture of 5.9 of 2-chloro-1-(4-nitrophenyl)hexan-3-one and 1.7 g of thioacetamide is heated at 90°-100° C. for 6 hours and then cooled and taken up with ethyl acetate. The precipitate formed is filtered off and washed with ethyl acetate and then with ether to give 5.6 g of 2-methyl-4-propyl-5-(4-nitrobenzyl)thiazole in the form of crystals melting at 124° C.

EXAMPLE 10

2-Methyl-4-propyl-5-(4-aminobenzyl)thiazole

Formula I: $R_1=CH_2CH_2CH_3$, $R_2=CH_3$, $R_3=NH_2$ 5.5 g of 2-methyl-4-propyl-5-(4-nitrobenzyl)thiazole in 60 ml of methanol are hydrogenated at normal pressure and room temperature in the presence of Raney nickel. After filtration of the catalyst and concentration of the filtrate, the residue is taken up with isopropyl ether, filtered off and then taken up in ethanol, passed over animal charcoal and concentrated to give 3.4 g of 2-methyl-4-propyl-5-(4-aminobenzyl)thiazole in the form of a greenish solid, which is used as such for the next step.

EXAMPLE 11

2-[4-(2-Methyl-4-propylthiazol-5-ylmethyl)-phenylaminocarbonyl]benzosulfonic acid Formula I: $R_1=CH_2CH_2CH_3$, $R_2=CH_3$,

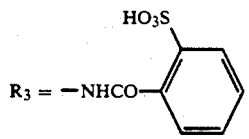

$R_3 = -NHCO-$ 3.4 g of 2-methyl-4-propyl-5-(4-aminobenzyl)thiazole are dissolved in 40 ml of acetonitrile and treated with a solution of 2.54 g of o-sulfobenzoic anhydride in 20 ml of acetonitrile. The mixture is stirred for 2 hours at 50° C. and methanol is then added until a divided solid in suspension is obtained. After cooling, the precipitate is filtered off to give 2.9 g of 2-[4-(2-methyl-4-propyl-thiazol-5-ylmethyl)phenylaminocarbonyl]benzosulfonic acid in the form of a white powder melting at 293°–4° C.

EXAMPLE 12

Ethyl 4-(aminothiocarbonylmercapto)butyrate

Formula VI: $R_2=S(CH_2)_3COOEt$

A mixture of 10 g of ammonium dithiocarbamate (i.e. 34 g of a 30% aqueous solution) and 17.7 g of ethyl 4-bromobutyrate in 70 ml of ethanol is stirred for 2 days at room temperature. The reaction medium is extracted with methylene chloride and the organic phase is dried and then concentrated to give 19 g of ethyl 4-(aminothiocarbonylmercapto)butyrate in the form of a semicrystalline yellow oil.

The solution of ammonium dithiocarbamate is obtained as follows: 30 g of carbon disulfide are dissolved in 200 ml of isopropyl acetate. A stream of ammonia is bubbled into the solution for 3 and a half hours, the temperature being kept at between 20 and 30° C. A substantial precipitate is observed. This is dissolved by the addition of an accurately weighed amount of about 100 g of water. The reaction medium is stirred and then decanted. The aqueous phase is recovered and weighed and the difference between this weight and the weight of water added corresponds to the ammonium dithiocarbamate (i.e. 42 g). This solution is kept in the cold and dark.

EXAMPLE 13

Ethyl 4-[[4-propyl-5-(4-nitrobenzyl)thiazol-2-yl]mercapto]butyrate

Formula VII: $V=NO_2$, $R_1=CH_2CH_2CH_3$, $R_2=S(CH_2)_3COOEt$

A mixture of 4 g of 2-chloro-1-(4-nitrophenyl)hexan-3-one and 3.7 g of ethyl 4-(aminothiocarbonylmercapto)butyrate is heated for 12 hours at 90°–100° C. It is then taken up with chloroform, the insoluble material is removed and the filtrate is concentrated to give a brown oil. After purification on a silica column (eluent: 6/4 ethyl acetate/cyclohexane), 3 g of ethyl 4-[[4-propyl-5-(4-nitrobenzyl)thiazol-2-yl]mercapto]butyrate are obtained in the form of an oil, which is used as such for the remaining operations.

EXAMPLE 14

Ethyl 4-[[4-propyl-5-(4-aminobenzyl)thiazol-2-yl]mercapto]butyrate

Formula I: $R_2=CH_2CH_2CH_3$, $R_2=S(CH_2)_3COOEt, R_3=NH_2$ 3 g of ethyl 4-[[4-propyl-5-(4-nitrobenzyl)thiazol-2-yl]mercapto]butyrate in 50 ml of ethanol are hydrogenated at normal pressure and room temperature in the presence of Raney nickel. After filtration of the catalyst and concentration of the filtrate, the brown oil obtained is taken up with acidified water. The aqueous phase is extracted with chloroform, rendered basic with dilute sodium hydroxide and extracted with ether. The ether solution is dried and concentrated to give a yellow oil, which is purified on a silica column (eluent: 7/3 cyclohexane/ethyl acetate) to give 0.6 g of ethyl 4-[[4-propyl-5-(4-aminobenzyl)thiazol-2-yl]mercapto]butyrate in the form of a pink oil.

EXAMPLE 15

Ethyl 4-[[4-propyl-5-(4-(2-sulfobenzoylamino)benzyl)thiazol-2-yl]mercapto]butyrate Formula I: $R_2=CH_2CH_2CH_3$, $R_2=S(CH_2)_3COOEt$,

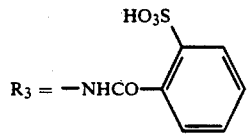

$R_3 = -NHCO-$ 0.6 g of ethyl 4-[[4-propyl-5-(4-aminobenzyl)thiazol-2-yl]mercapto]butyrate is dissolved in 20 ml of acetonitrile and treated with 0.3 g of o-sulfobenzoic anhydride. The mixture is stirred for 6 hours at room temperature and the precipitate formed is then filtered off to give 0.8 g of ethyl 4-[[4-propyl-5-(4-(2-sulfobenzoylamino)benzyl)thiazol-2-yl]mercapto ]butyrate in the form of a white powder melting at 97°–8° C.

EXAMPLE 16

Methoxythioacetamide

Formula VI: $R=CH_2OCH_3$

A mixture of 25 g of methoxyacetonitrile, 35 ml of pyridine and 25 ml of triethylamine is treated with a stream of $H_2S$ for 4 hours. The reaction is exothermic and it is necessary to cool the mixture in order to keep it at room temperature. When the reaction is complete, the reaction mixture is poured into a saturated solution of sodium chloride and then extracted with ether. The ether phase is washed with acidified water and then with water. After drying and concentration of the solvent, the orange oil obtained is taken up in cold petroleum ether and the precipitate formed is filtered off to give 28.8 g of methoxythioacetamide in the form of crystals melting at 63°–4° C.

EXAMPLE 17

2-Methoxymethyl-4-propyl-5-(4-nitrobenzyl)thiazole

Formula VII: $R_1$=CH$_2$CH$_2$CH$_3$, $R_2$=CH$_2$OCH$_3$, V=NO$_2$

A mixture of 1.2 g of methoxythioacetamide and 3 g of 2-chloro-1-(4-nitrophenyl)hexan-3-one is heated at 90°–100° C. for 4 hours and then cooled and taken up with ethyl acetate. The solution obtained is passed over animal charcoal and then evaporated. The brown oil obtained is purified on a silica column (eluent: 6/4 cyclohexane/ethyl acetate) to give 0.9 g of 2-methoxymethyl-4-propyl-5-(4-nitrobenzyl)thiazole in the form of a brown oil, which is used as such for the next step.

EXAMPLE 18

2-Methoxymethyl-4-propyl-5-(4-aminobenzyl)thiazole

Formula I: $R_1$=CH$_2$CH$_2$CH$_3$, $R_2$=CH$_2$OCH$_3$, $R_3$=NH$_2$ 0.9 of 2-methoxymethyl-4-propyl-5-(4-nitrobenzyl)thiazole in 50 ml of methanol is hydrogenated at normal pressure and room temperature in the presence of Raney nickel. After filtration of the catalyst and concentration of the filtrate, the brown oil obtained is taken up with acidified water. The aqueous phase is extracted with ether, rendered basic with dilute sodium hydroxide and extracted with ethyl acetate. The organic phase is dried and concentrated to give 0.5 g of 2-methoxymethyl-4-propyl-5-(4-aminobenzyl)thiazole in the form of an orange oil, which is used as such for the next step.

EXAMPLE 19

2-[4-(2-Methoxymethyl-4-propylthiazol-5-yl-methyl)-phenylaminocarbonyl]benzosulfonic acid Formula I: $R_1$=CH$_2$CH$_2$CH$_3$, $R_2$=CH$_2$OCH$_3$,

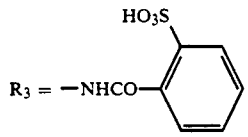

0.5 g of 2-methoxymethyl-4-propyl-5-(4-aminobenzyl)thiazole is dissolved in 50 ml of acetonitrile and treated with 0.3 g of o-sulfobenzoic anhydride. The mixture is stirred for 6 hours at room temperature and the precipitate formed is then filtered off to give 0.5 g of 2-[4-(2-methoxymethyl-4-propylthiazol-5-yl-methyl)-phenylaminocarbonyl]benzosulfonic acid in the form of a beige powder melting at 242.5° C.

EXAMPLE 20

Methyl (4-propyl-5-(4-nitrobenzyl)thiazol-2-yl)aminoacetate

Formula VII: $R_1$=CH$_2$CH$_2$CH$_3$, $R_2$=NHCH$_2$COOMe, V=NO$_2$

A mixture of 2.5 g of 3-chloro-4-(4-nitrophenyl)butan-2-one and 1.3 g of N-carboxymethylthiourea is heated at 90°–100° C. for 4 hours and then cooled and taken up with ethyl acetate. The precipitate formed is filtered off and washed with ethyl acetate and then with ether. It is then dissolved in 30 ml of methanol, and 1 ml of thionyl chloride is added dropwise. The reaction medium is refluxed for 6 hours, the solvent is then evaporated off and the residue is taken up with acidified water. The aqueous phase is rendered basic with sodium bicarbonate and extracted with ether. After drying and concentration of the ether, the yellow solid is taken up with petroleum ether and filtered off to give 2.7 g of methyl (4-propyl-5-(4-nitrobenzyl)thiazol-2-yl)aminoacetate in the form of a yellow powder melting at 105° C.

EXAMPLE 21

(4-propyl-5-(4-aminobenzyl)thiazol-2-yl)aminoacetate

Formula I: $R_1$=CH$_2$CH$_2$CH$_3$, $R_2$=NHCH$_2$COOMe, $R_3$=NH$_2$ 2.6 g of methyl (4-propyl-5-(4-nitrobenzyl)thiazol-2-yl)aminoacetate in 60 ml of methanol are hydrogenated at normal pressure and room temperature in the presence of Raney nickel. After filtration of the catalyst and concentration of the filtrate, the residue is taken up with acidified water. The aqueous phase is extracted with ether, rendered basic with sodium carbonate and extracted with ethyl acetate. After drying and concentration, the residue is taken up with pentane to give 1.8 g of methyl (4-propyl-5-(4-aminobenzyl)thiazol-2-yl)aminoacetate in the form of a beige solid melting at 106° C.

EXAMPLE 22

Methyl (4-propyl-5-(4-(2-sulfobenzoylamino)benzyl)thiazol-2-yl)aminoacetate

Formula I: $R_1$=CH$_2$CH$_2$CH$_3$, $R_2$=NHCH$_2$COOMe,

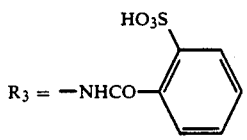

1.8 g of methyl (4-propyl-5-(4-aminobenzyl)thiazol-2-yl)aminoacetate are dissolved in 40 ml of acetonitrile and treated with a solution of 1.08 g of o-sulfobenzoic anhydride in 10 ml of acetonitrile. The mixture is stirred for 24 hours at 25° C., the solution is then concentrated, the residue is taken up with ethyl acetate and the precipitate is filtered off. It is chromatographed on a silica column in the presence of triethylamine to give 1.9 g of the triethylamine salt of methyl (4-propyl-5-(4-(2-sulfobenzoylamino)benzyl)thiazol-2-yl)aminoacetate in the form of a white powder melting at 95°–6° C.

EXAMPLE 23

Methyl thioacetamidoacetate

Formula VI: $R_2$=CH$_2$CO$_2$CH$_3$

A stream of H$_2$S is bubbled into a mixture of methyl cyanoacetate (70 g, 710 mmol), pyridine (70 ml, 710 mmol) and triethylamine (49.6 ml, 350 mmol). The exothermic reaction, which is cooled with an ice bath, is followed by TLC. When the reaction is complete, the reaction mixture is washed with a dilute solution of acid and extracted with ether. After drying over magnesium sulfate and concentration under vacuum, an orange oil is obtained which crystallizes. The yellow solid obtained is washed with ether and then filtered off to give 83.3 g of methyl thioacetamidoacetate melting at 78°–9° C.

EXAMPLE 24

2-Methoxycarbonylmethyl-5-(4-nitrobenzyl)-4-propylthiazole

Formula VII: $R_1=CH_2CH_2CH_3$, $R_2=CH_2CO_2CH_3$, $V=NO_2$

An equimolar mixture (13 mmol) of 2-chloro-1-(4-nitrophenyl)hexan-3-one and methyl thioacetamidoacetate is heated at 60° C. for 24 hours. The reaction mixture is taken up in methylene chloride, stirred for ten minutes and filtered. The filtrate is concentrated and the residue is taken up in isopropyl ether to give 2.8 g of 2-methoxycarbonylmethyl-5-(4-nitrobenzyl)-4-propylthiazole, which is a yellow powder melting at 102° C.

EXAMPLE 25

2-Methoxycarbonylmethyl-5-(4-aminobenzyl)-4-propylthiazole

Formula I: $R_1=CH_2CH_2CH_3$, $R_2=CH_2CO_2CH_3$, $R_3=NH_2$ 2.7 g of 2-methoxycarbonylmethyl-5-(4-nitrobenzyl)-4-propylthiazole (8.1 mmol) in 50 ml of methanol are hydrogenated at room temperature under 1 atmosphere in the presence of 3 g of Raney nickel. The reaction mixture is filtered and then concentrated to give 2 g of the amine derivative in the form of a brown oil.

EXAMPLE 26

2-[4-2-Methoxycarbonylmethyl-4-propylthiazol-5-ylmethyl)phenylaminocarbonyl]benzosulfonic acid Formula I: $R_1=CH_2CH_2CH_3$, $R_2=CH_2,CO_2,CH_3$,

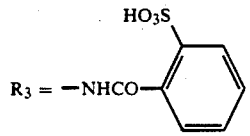

$R_3 = $ —NHCO—

A solution of 2 g of 2-methoxycarbonylmethyl-5-(4-aminobenzyl)-4-propylthiazole (5.6 mmol) in 20 ml of acetonitrile is treated with a solution of 1.06 g of o-sulfobenzoic anhydride in 10 ml of acetonitrile at room temperature. The reaction mixture is stirred for one day at this temperature and then concentrated under vacuum. The brown oil obtained is taken up in methanol to give 300 mg of 2-[4-(2-methoxycarbonylmethyl-4-propylthiazol-5-ylmethyl) phenylaminocarbonyl]benzosulfonic acid, which is a beige powder melting at 203° C.

EXAMPLE 27

2-Ethoxycarbonylaminothioacetamide

Formula VI: $R_2=CH_2NHCO_2CH_2CH_3$ 61 ml of triethylamine (0.44 mol) are added to a solution of 20 g of aminoacetonitrile hydrochloride (0.22 mol) in a tetrahydrofuran/chloroform mixture (1/1 v/v). 21 ml of ethyl chloroformate (0.22 mol) are then added dropwise. The reaction medium is stirred for 8 hours at room temperature and 1 hour at 50° C. and filtered. The filtrate is concentrated and the residue is washed with water and extracted with chloroform. After drying over magnesium sulfate, filtration and concentration, 27.5 g of ethoxycarbonylaminoacetonitrile, which is a brown liquid, are obtained.

A stream of $H_2S$ is passed into a mixture of 27.5 g of ethoxycarbonylaminoacetonitrile (210 mmol), pyridine (21ml, 210 mmol) and triethylamine (14.5 ml, 105 mmol) according to the procedure of Example 23. After stirring for 4 hours at room temperature and washing with water, a beige precipitate is obtained which is filtered off to give 6.6 g of ethoxycarbonylaminothioacetamide, which is a beige powder melting at 116° C.

EXAMPLE 28

2-Ethoxycarbonylaminomethyl-5-(4-nitrobenzyl)-4-propylthiazole

Formula VII: $R_1=CH_2CH_2CH_3$, $R_2=CH_2NHCO_2CH_2CH_3$, $V=NO_2$

An equimolar mixture (19.6 mmol) of 2-chloro-1-(4-nitrophenyl)hexan-3-one and ethoxycarbonylaminothioacetamide is heated at 90° C. for 12 hours. The reaction mixture is taken up with ethyl acetate. The precipitate obtained (4.8 g) is filtered off and consists only of the desired derivative 2-ethoxycarbonylaminomethyl-5-(4-nitrobenzyl)-4-propylthiazole melting at 118° C.

EXAMPLE 29

2-Ethoxycarbonylaminomethyl-5-(4-aminobenzyl)-4-propylthiazole

Formula I: $R_1=CH_2CH_2CH_3$, $R_2=CH_2NHCO_2CH_2CH_3$, $R_3=NH_2$ 4.7 g of 2-ethoxycarbonylaminomethyl-5-(4-nitrobenzyl)-4-propylthiazole (13 mmol) in 100 ml of ethanol are hydrogenated at room temperature under 1 atmosphere in the presence of 5 g of Raney nickel. The reaction mixture is filtered and then concentrated to give 2 g of 2-ethoxycarbonylaminomethyl-5-(4-aminobenzyl)-4-propylthiazole in the form of a beige powder melting at 126° C.

EXAMPLE 30

2-[4-(2-Ethoxycarbonylaminomethyl-4-propylthiazol-5-ylmethyl)phenylaminocarbonyl]benzosulfonic acid Formula I: $R_1CH_2CH_2CH_2$, $R_2=CH_2NHCO_2CH_2CH_3$,

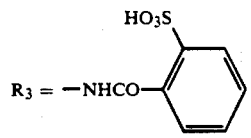

$R_3 = $ —NHCO—

A solution of 2.9 g of 2-ethoxycarbonylaminomethyl-5-(4-aminobenzyl)-4-propylthiazole (8.7 mmol) in 50 ml of tetrahydrofuran is treated with 1.6 g of o-sulfobenzoic anhydride added in small portions, at room temperature. The reaction mixture is stirred for one day at this temperature and then concentrated under vacuum. The precipitate formed is filtered off and washed with ethyl acetate and then with ether. The solid obtained is purified by chromatography on silica gel (9/1/0.5 isopropanol/acetone/triethylamine) to give an orange oil, which is taken up in acidified water. This gives a white precipitate, which is filtered off and washed with acetone and consists only of 2-[4-(2-ethoxycarbonylaminomethyl-4-propylthiazol-5-ylmethyl) phenylaminocarbonyl]benzosulfonic acid melting at 189° C.

EXAMPLE 31

2-Amino-5-(4-nitrobenzyl)-4-propylthiazole

Formula VII: $R_1=CH_2CH_2CH_3$, $R_2=NH_2$, $V=NO_2$

An equimolar mixture (19.6 mmol) of 2-chloro-1-(4-nitrophenyl)hexan-3-one and thiourea is heated at 60° C. for 6 hours. The reaction mixture is taken up in methylene chloride and the pale yellow precipitate obtained is filtered off. After recrystallization from CH₃CN, 4.7 g of the derivative 2-amino-5-(4-nitrobenzyl)-4-propylthiazole are obtained in the form of beige crystals melting at 156° C.

EXAMPLE 32

2-Amino-5-(4-aminobenzyl)-4-propylthiazole

Formula I: $R_1=CH_2CH_2CH_2$, $R_2=NH_2$, $R_3=NH_2$ 4.0 g of 2-amino-5-(4-nitrobenzyl)-4-propylthiazole (13 mmol) in 100 ml of ethanol are hydrogenated according to Example 25. 1.9 g of 2-amino-5-(4-aminobenzyl)-4-propylthiazole are obtained in the form of a brown oil.

EXAMPLE 33

2-[4-(2-Amino-4-propylthiazol-5-ylmethyl)-phenylaminocarbonyl]benzosulfonic acid Formula I: $R_1=CH_2CH_2CH_3$, $R_2=NH_2$,

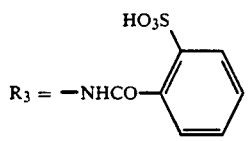

$R_3 = $

A solution of 2.0 g of 2-amino-5-(4-aminobenzyl)-4-propylthiazole (8.08 mmol) in 50 ml of tetrahydrofuran is treated with 1.5 g of o-sulfobenzoic anhydride added in small portions, at room temperature. The reaction mixture is stirred for one day at this temperature and then concentrated under vacuum. It is taken up in a methanol/ethyl acetate mixture. The insoluble material filtered off consists only of 2-[4-(2-amino-4-propylthiazol-5-ylmethyl)phenylaminocarbonyl ]benzosulfonic acid melting at 253° C.

EXAMPLE 34

2-Acetamido-5-(4-nitrobenzyl)-4-propylthiazole

Formula VII: $R_1=CH_2CH_2CH_3$, $R_2=NHCOCH_3$, $V=NO_2$ 2 g (7.2 mmol) of 2-amino-5-(4-nitrobenzyl)-4-propylthiazole in 2.5 ml of acetic anhydride, in the presence of 88 mg of 4-dimethylaminopyridine (0.72 mmol), are heated at 80° C. for 1 hour. As the reaction mixture is cooled, the formation of a precipitate is observed. This is filtered off and washed with ether to give 1.6 g of the derivative 2-acetamido-5-(4-nitrobenzyl)-4-propylthiazole, which is pale yellow solid melting at 170° C.

EXAMPLE 35

2-Acetamido-5-(4-aminobenzyl)-4-propylthiazole

Formula I: $R_1=CH_2CH_2CH_3$, $R_2=NHCOCH_3$, $R_3=NH_2$ 1.6 g of 2-acetamido-5-(4-nitrobenzyl)-4-propylthiazole (5 mmol) are hydrogenated at room temperature according to Example 25. The reaction mixture is filtered and then concentrated to give 1.3 g of 2-acetamido-5-(4-aminobenzyl)-4-propylthiazole in the form of a pale yellow solid melting at 146° C.

EXAMPLE 36

2-[4-(2-Acetamido-4-propylthiazol-5-yl-methyl)-phenylaminocarbonyl]benzosulfonic acid Formula I: $R_1=CH_2CH_2CH_3$, $R_2=NHCOCH_3$,

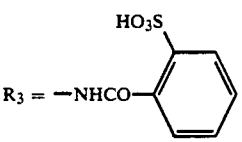

$R_3 = $ —NHCO—

A solution of 1.3 g of 2-acetamido-5-(4-aminobenzyl)-4-propylthiazole (4.5 mmol) in 50 ml of acetonitrile is treated with a solution of 0.8 g of o-sulfobenzoic anhydride in 10 ml of acetonitrile at room temperature. The reaction mixture is stirred for one day at this temperature and then concentrated under vacuum. The precipitate formed is filtered off, washed with ether and then purified by acid-base conversion to give 1.19 g of 2-[4-(2-acetamido-4-propylthiazol-5-yl-methyl)-phenylaminocarbonyl]benzosulfonic acid in the form of a whitish powder melting at 195° C.

EXAMPLE 37

2-Chloro-1-(4-nitrophenyl)octan-3-one

Formula IV: $R_1=CH_2CH_2CH_2CH_2CH_3$, $V=NO_2$

2-Chloro-1-(4-nitrophenyl)octan-3-one is prepared by the procedure of Example 1. The red oil obtained after concentration of the reaction mixture is purified by chromatography on a silica gel column (7/3 chloroform/cyclohexane) and crystallizes with a melting point of 118°–120° C.

EXAMPLE 38

2-Methyl-5-(4-nitrobenzyl)-4-pentylthiazole

Formula VII: $R_1=CH_2CH_2CH_2CH_2CH_3$, $R_2=CH_3$, $V=NO_2$

An equimolar mixture (19.6 mmol) of 2-chloro-1-(4-nitrophenyl)octan-3-one and thioacetamide is heated at 60° C. for 24 hours. After cooling to room temperature, the reaction mixture is concentrated and taken up in isopropyl ether to give 1.7 g of 2-methyl-5-(4-nitrobenzyl)-4-pentylthiazole, which is a pale yellow solid melting at 57° C.

EXAMPLE 39

2-Methyl-5-(4-aminobenzyl)-4-pentylthiazole

Formula I: $R_1=CH_2CH_2CH_2CH_2CH_3$, $R_2=CH_3$, $R_3=NH_2$ 1.7 g of 2-methyl-5-(4-nitrobenzyl)-4-pentylthiazole (5.6 mmol) in 100 ml of ethanol are hydrogenated according to Example 25 to give 1.4 g of 2-methyl-5-(4-aminobenzyl)-4-pentylthiazole in the form of a colorless oil.

EXAMPLE 40

2-[4-(2-Methyl-4-pentylthiazol-5-ylmethyl)-phenylaminocarbonyl]benzosulfonic acid Formula I: $R_1=CH_2CH_2CH_2CH_2CH_3$, $R_2=CH_3$,

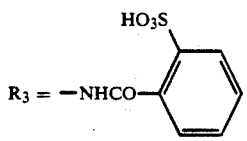

1.4 g of 2-methyl-5-(4-aminobenzyl)-4-pentylthiazole (5.1 mmol) and 0.9 g of o-sulfobenzoic anhydride are reacted according to the procedure of Example 26. The reaction mixture is stirred for one day at room temperature. After concentration, a beige solid is obtained which is triturated in ether. The solid is taken up in water rendered basic with $Na_2CO_3$. After washing with ether, the aqueous phase is acidified again by the passage of a stream of $SO_2$. The product is then extracted with chloroform. After drying and concentration, 1.7 g of 2-[4-(2-methyl-4-pentylthiazol-5-ylmethyl)-phenylaminocarbonyl]benzosulfonic acid are obtained in the form of a whitish powder melting at 157°–158° C.

EXAMPLE 41

2-[4-(2-Amino-4-propylthiazol-5-ylmethyl)-phenylaminocarbonyl]-3,6-dichlorobenzoic acid Formula I: $R_1=CH_2CH_2CH_3$, $R_2=NH_2$,

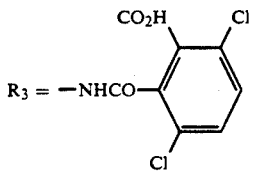

1.9 g of 2-amino-5-(4-aminobenzyl)-4-propylthiazole (7.65 mmol) and 1.7 g of 3,6-dichlorophthalic anhydride are reacted under the conditions of Example 26. The reaction mixture is stirred for one day at room temperature. After concentration, a beige solid is obtained which is triturated in ether to give 2.2 g of 2-[4-(2-amino-4-propylthiazol-5-ylmethyl)phenylaminocarbonyl]-3,6-dichlorobenzoic acid in the form of a beige powder melting at 153° C.

EXAMPLE 42

2-Amino-5-(4-nitrobenzyl)-4-pentylthiazole

Formula VII: $R_1=CH_2CH_2CH_2CH_2CH_3$, $R_2=NH_2$, $V=NO_2$

An equimolar mixture (18 mmol) of 2-chloro-1-(4-nitrophenyl)octan-3-one and thiourea is heated at 60° C. for 6 hours. The reaction mixture is taken up in methylene chloride and filtered. After concentration, the filtrate is washed with water which has been rendered basic, and extracted with chloroform to give 3 g of 2-amino-5-(4-nitrobenzyl)-4-pentylthiazole in the form of a brown oil, which is used as such for the next step.

EXAMPLE 43

2-Amino-5-(4-aminobenzyl)-4-pentylthiazole

Formula I: $R_1=CH_2CH_2CH_2CH_2CH_3$, $R_2=NH_2$ 3.0 g of 2-amino-5-(4-nitrobenzyl)-4-pentylthiazole (9.8 mmol) in 100 ml of ethanol are hydrogenated according to Example 25 to give 3 g of 2-amino-5-(4-aminobenzyl)-4-pentylthiazole in the form of a brown oil.

EXAMPLE 44

2-[4-(2-Amino-4-pentylthiazol-5-ylmethyl)-phenylaminocarbonyl]benzosulfonic acid Formula I: $R_1=CH_2CH_2CH_2CH_2CH_3$, $R_2=NH_2$,

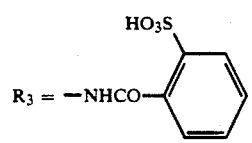

3 g of 2-amino-5-(4-aminobenzyl)-4-pentylthiazole (10 mmol) and 2 g of o-sulfobenzoic anhydride are reacted under the conditions of Example 26. The reaction mixture is stirred for one day at room temperature. After concentration, a pinkish solid is obtained which is triturated in ether to give 2.1 g of 2-[4-(2-amino-4-pentylthiazol-5-ylmethyl)phenylaminocarbonyl]benzosulfonic acid in the form of a crystalline powder melting at 266° C.

EXAMPLE 45

2-Methoxymethyl-5-(4-nitrobenzyl)-4-pentylthiazole

Formula VII: $R_1=CH_2CH_2CH_2CH_2CH_3$, $R_2=CH_2OCH_3$, $V=NO_2$

A mixture of 5 g of 2-chloro-1-(4-nitrophenyl)octan-3-one (18 mmol) and 2.8 g of methoxythioacetamide (27 mmol) is heated at 60° C. for 12 hours. The reaction medium is taken up in methylene chloride and filtered. After concentration, the filtrate is washed with a 2N solution of NaOH and extracted with chloroform. After drying over magnesium sulfate and concentration, 4 g of 2-methoxymethyl-5-(4-nitrobenzyl)-4-pentylthiazole are obtained in the form of an orange oil.

EXAMPLE 46

2-Methoxymethyl-5-(4-aminobenzyl)-4-pentylthiazole

Formula I: $R_1=CH_2CH_2CH_2CH_2CH_3$, $R_2=CH_2OCH_3$, $R_3=NH_2$ 4 g of 2-methoxymethyl-5-(4-nitrobenzyl)-4-pentylthiazole (0.012 mol) are hydrogenated according to the procedure of Example 25 to give 3.4 g of 2-methoxymethyl-5-(4-aminobenzyl)-4-pentylthiazole in the form of a brown oil.

EXAMPLE 47

2-[4-(2-Methoxymethyl-4-pentylthiazol-5-yl)phenylaminocarbonyl]benzosulfonic acid Formula I: $R_1=CH_2CH_2CH_2CH_2CH_3$, $R_2=CH_2OCH_3$,

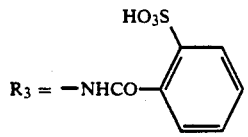

3.4 of 2-methoxymethyl-5-(4-aminobenzyl)-4-pentylthiazole (0.01 mol) and 1.9 g of o-sulfobenzoic anhydride are treated under the conditions of Example 26. After concentration of the reaction medium and trituration in ether, 4.7 g of a brown powder are obtained which is purified by acid-base conversion and extraction with ethyl acetate to give 4 g of 2-[4-(2-methoxymethyl-4-pentylthiazol-5-yl) phenylaminocarbonyl]-benzosulfonic acid in the form of a light beige powder melting at 216°–217° C.

EXAMPLE 48

(Methylthio)thioacetamide

Formula VI: $R_2=CH_2SCH_3$ $H_2S$ is bubbled for 6 hours into a mixture of 25 g (0.29 mol) of methylthioacetonitrile, 30 ml (0.37 mol) of pyridine and 20.2 ml (0.145 mol) of triethylamine at 0° C. The reaction medium is then poured into a cooled dilute solution of acid and extracted with ether. After drying over magnesium sulfate and concentration, a green oil is obtained which crystallizes. The solid is taken up in isopropyl ether. 22 g of greyish-green crystals melting at 65° C. are finally obtained.

EXAMPLE 49

2-Methylthiomethyl-5-(4-nitrobenzyl)-4-propylthiazole

Formula VII: $R_2=CH_2SCH_3$, $R_1=CH_2CH_2CH_3$, $V=NO_2$

A mixture of 5 g of 2-chloro-1-(4-nitrophenyl)-hexan-3-one (0.02 mol) and 2.6 g of (methylthio)thioacetamide (0.022 mol) is heated at 60° C. for 24 h. The reaction is followed by TLC (7/3 cyclohexane/ethyl acetate). The reaction medium is then treated according to the process of Example 45 to give 5.6 g of 2-methylthiomethyl-5-(4-nitrobenzyl)-4-propylthiazole in the form of an orange oil.

EXAMPLE 50

2-Methylthiomethyl-5-(4-aminobenzyl)-4-propylthiazole

Formula I: $R_1=CH_2CH_2CH_3$, $R_2CH_2SCH_3$, $R_3=NH_2$ 5.6 g of 2-methylthiomethyl-5-(4-nitrobenzyl)-4-propylthiazole (0.017 mol) are hydrogenated according to the procedure of Example 25 to give a 1:1 mixture of 2-methyl-5-(4-aminobenzyl)-4-propylthiazole and 2-methylthiomethyl-5-(4-aminobenzyl)-4-propylthiazole, which is separated by chromatography on silica (eluent: 95/5 methylene chloride/ethyl acetate). 1.3 g of 2-methylthiomethyl-5-(4-aminobenzyl)-4-propylthiazole are finally obtained in the form of a brown oil, which is used as such for the next step.

EXAMPLE 51

2-[4-(2-Methylthiomethyl-4-propylthiazol-5-ylmethyl)-phenylaminocarbonyl]benzosulfonic acid Formula I: $R_1=CH_2CH_2CH_3$, $R_2=CH_2SCH_3$,

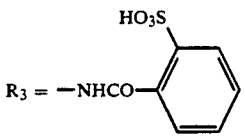

1.3 g (3.7 mmol) of 2-methylthiomethyl-5-(4-aminobenzyl)-4-propylthiazole and 700 mg of o-sulfobenzoic anhydride are treated according to the procedure of Example 26. The reaction medium is stirred at room temperature for 6 hours. It is then filtered and the pale yellow solid obtained is rinsed with ether to give 1.7 g of 2-[4-(2-methylthiomethyl-4-propylthiazol-5-ylmethyl)phenylaminocarbonyl]benzosulfonic acid melting at 254°–256° C.

EXAMPLE 52

2-(2-Chlorophenyl)-5-(4-nitrobenzyl)-4-propylthiazole

Formula VII: $R_1=CH_2CH_2CH_3$, $R_2=$2-chlorophenyl, $V=NO_2$

An equimolecular mixture (11.7 mmol) of 2-chloro-1-(4-nitrophenyl)hexan-3-one, prepared in Example 8, and 2-chlorothiobenzamide, prepared from 2-chlorobenzonitrile by bubbling $H_2S$ in the presence of triethanolamine, is heated at 60° C. for 8 hours, the reaction being followed by TLC (eluent: chloroform). The reaction mixture is then taken up with chloroform and filtered. The filtrate is washed with a saturated aqueous solution of sodium chloride. After drying and concentration of the organic phase, a brown oil is obtained which crystallizes from an ether/petroleum ether mixture. After filtration, 2.9 g of 2-(2-chlorophenyl)-5-(4-nitrobenzyl)-4-propylthiazole are obtained in the form of a yellow powder melting at 77°–80° C.

EXAMPLE 53

2-(2-Chlorophenyl) 5-(4-aminobenzyl)-4-propylthiazole

Formula I: $R_1=CH_2CH_2CH_3$, $R_2=$2-chlorophenyl, $R=NH_2$ 2 g (5.4 mmol) of 2-(2-chlorophenyl)-5-(4-nitrobenzyl)-4-propylthiazole are hydrogenated according to the process of Example 25.

1.8 g of 2-(2-chlorophenyl)-5-(4-aminobenzyl)-4-propylthiazole are obtained in the form of a brown oil, which crystallizes from an ether/petroleum ether mixture in the form of a yellow powder melting at 75°–77° C.

EXAMPLE 54

2-[4-[2-(2-Chlorophenyl)-4-propylthiazol-5-ylmethyl]-phenylaminocarbonyl]benzosulfonic acid Formula I: $R_1=CH_2CH_2CH_3$, $R_2=$2-chlorophenyl,

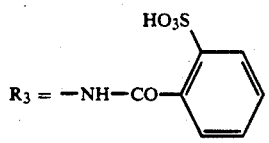

300 mg of 2-(2-chlorophenyl)-5-(4-aminobenzyl)-4-propylthiazole and 200 mg of o-sulfobenzoic anhydride are treated according to the process of Example 26 in an acetonitrile/tetrahydrofuran mixture. The reaction mixture is stirred at room temperature for 6 hours. It is then evaporated to dryness under vacuum. The cream solid obtained is washed with acetonitrile and then with ether and dried to give 400 mg of 2-[4-[2-(2-chlorophenyl)-4-propylthiazol-5-ylmethyl] phenylaminocarbonyl]benzosulfonic acid in the form of a beige powder melting at 143°–145° C.

PHARMACOLOGY

I. Principle

The affinity of the products of the Examples for angiotensin II receptors is evaluated by the technique of displacing a radioligand specifically bound to rat adrenal angiotensin II receptors.

II. Procedure

An aliquot of a rat adrenal gland homogenate incubates in the presence of a single concentration of $[^{125}I]$-SIAII (Sar$^1$,Tyr$^4$,Ile$^8$-angiotensin II), which is an angiotensin II receptor antagonist, and two concentrations of competing agents ($10^{-5}M$, $10^{-7}M$) for 60 min at 25° C.

The reaction is completed by the addition of a buffer, followed by rapid filtration through glasspaper filters. The non-specific binding is determined in the presence of angiotensin II.

III. Expression of the results

The results are expressed, for the concentrations tested, as the percentage displacement of the radioligand specifically bound to the adrenal angiotensin II receptors.

| Product of Example | IV. Results % displacement of the labeled ligand | |
|---|---|---|
| | 1E-5M | 1E-7M |
| 4 | 58 | 0 |
| 7 | 35 | 0 |
| 11 | 94 | 59 |
| 15 | 79 | 0 |
| 19 | 89 | 55 |
| 22 | 89 | 5 |
| 26 | 86 | 22 |
| 30 | 84 | 29 |
| 33 | 85 | 27 |
| 36 | 84 | 3 |
| 40 | 88 | 59 |
| 41 | 87 | 9 |
| 44 | 91 | 44 |

TOXICOLOGY

The products of the Examples described have an excellent tolerance after oral administration.

Their 50% lethal dose in rats was found to be greater than 300 mg/kg.

CONCLUSION

The products of the Examples described have a good affinity for angiotensin II receptors. In this respect, they may be used beneficially for the various pathological conditions in which angiotensin II is involved, in particular for the treatment of arterial hypertension and cardiac insufficiency, in dosages of 1 to 400 mg by oral administration and 0.01 to 50 mg by intravenous administration, in one or more dosage units per day.

What is claimed is:

1. A thiazole compound of the formula

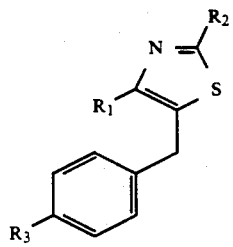

wherein:
$R_1$ is a lower alkyl radical having 1 to 6 carbon atoms or a $C_3$–$C_7$ cycloalkyl radical;
$R_2$ is a hydrogen atom, a halogen atom, a lower alkyl radical having 1 to 6 carbon atoms, a lower halogenoalkyl radical having 1 to 6 carbon atoms, a $C_3$–$C_7$ cycloalkyl radical, a phenyl radical or an heteroaromatic ring selected from the group consisting of heteroaromatic rings having 5 to 7 atoms and containing at least one nitrogen, oxygen or sulfur atom in the ring, optionally substituted by a lower alkyl group, a halogen, a halogenoloweralkyl group, a loweralkoxy group or a thioloweralkyloxy group;
$R_2$ can also be X—$(CH_2)_n$—CN, X—$(CH_2)_n$—COOR$_4$, X—$(CH_2)_n$—OR$_4$, X—$(CH_2)_n$—SR$_4$ or X—$(CH_2)_n$—CONR'R", wherein X is a bond, a sulfur atom or a group NH, n is an integer from 0 to 5, $R_4$ is a hydrogen atom, a lower alkyl radical having 1 to 6 carbon atoms, a lower halogenoalkyl radical having 1 to 6 carbon atoms or a $C_3$–$C_7$ cycloalkyl radical, $R_5$ is defined in the same way as $R_4$ can also be phenyl, a heteroaromatic ring as defined above or methanebiphenyl, and R' and R" are independently a hydrogen atom, a lower alkyl radical having 1 to 6 carbon atoms or a $C_3$–$C_7$ cycloalkyl radical or they can form, together with the nitrogen atom to which they are attached, a heterocycle selected from the group consisting of pyrrolidine, piperidine, morpholine, thiomorpholine, piperazine and N-substituted piperazine wherein the N-substituent is a lower alkyl radical having 1 to 6 carbon atoms, phenyl or a heteroaromatic ring as defined above; and
r$_3$ is a nitro or amino group or one of the following groups:

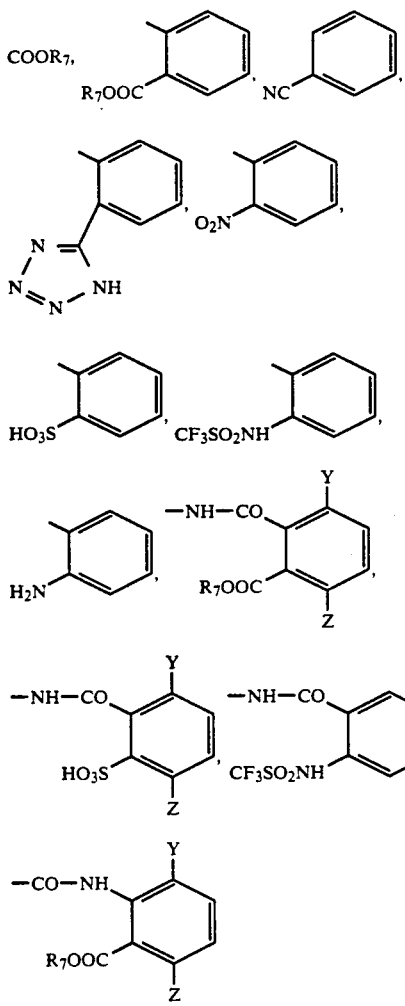

in which $R_7$ is a hydrogen atom, a lower alkyl radical having 1 to 6 carbon atoms or a benzyl radical and Y and Z are independently a hydrogen atom, a halogen atom, a lower alkyl radical having 1 to 6 carbon atoms, an O-lower alkyl radical or trifluoromethyl;

or a pharmaceutically acceptable addition salt thereof.

2. A thiazole compound of the formula

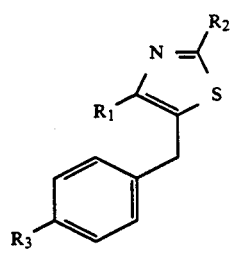

wherein:

$R_1$ is a lower alkyl radical having 1 to 6 carbon atoms or a $C_3$-$C_7$ cycloalkyl radical;

$R_2$ is a hydrogen atom, a halogen atom, a lower alkyl radical having 1 to 6 carbon atoms, a lower halogenoalkyl radical having 1 to 6 carbon atoms, a $C_3$-$C_7$ cycloalkyl radical, phenyl or a heteroaromatic ring selected from the group consisting of heteroaromatic rings having 5 to 7 carbon atoms and containing at least one nitrogen, oxygen or sulfur atom in the ring, optionally substituted by a loweralkyl group, a halogen, a halogenoloweralkyl group, a loweralkoxy group or a thioloweralkoxy group;

$R_2$ can also be $X-(CH_2)_n-CN$, $X-(CH_2)_n-COOR_4$, $X-(CH_2)_n-OR_4$, $X-(CH_2)_n-SR_4$, $X-(CH_2)_n-NR'R''$, $X-(CH_2)_n-CONR'R''$ or $X-(CH_2)_n-NH-COR_5$, wherein X is a bond, a sulfur atom or a group NH, n is an integer from 0 to 5, $R_4$ is a hydrogen atom, a lower alkyl radical having 1 to 6 carbon atoms, a lower halogenoalkyl radical having 1 to 6 carbon atoms or a $C_3$-$C_7$ cycloalkyl radical, $R_5$ is defined in the same way as $R_4$ but can also be a phenyl radical, a heteroaromatic ring as defined above or methanebiphenyl, and R' and R'' are independently a hydrogen atom, a lower alkyl radical having 1 to 6 carbon atoms or a $C_3$-$C_7$ cycloalkyl radical or they can form, together with the nitrogen atom to which they are attached, a heterocycle selected from the group consisting of pyrrolidine, piperidine, morpholine, thiomorpholine piperazine and N-substituted piperazine wherein the N-substituent is a lower alkyl radical having 1 to 6 carbon atoms, phenyl or a heteroaromatic ring as defined above; and $R_3$ is one of the following groups:

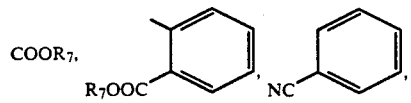

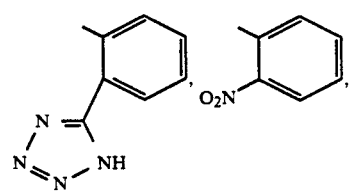

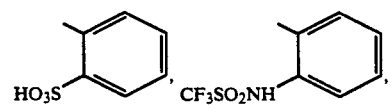

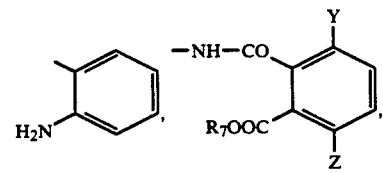

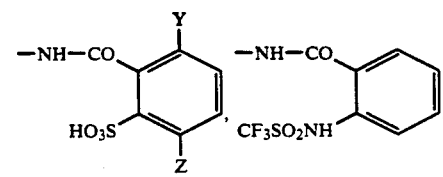

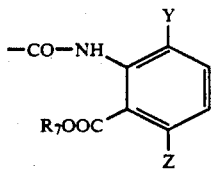

wherein R₇ is a hydrogen atom, a lower alkyl radical having 1 to 6 carbon atoms or a benzyl radical and Y and Z are independently a hydrogen atom, a halogen atom, a lower alkyl radical having 1 to 6 carbon atoms, an O-lower alkyl radical or a trifluoromethyl;

or a pharmaceutically acceptable addition salt thereof.

3. A thiazole compound according to claim 1 or 2, wherein $R_1$ is an n-propyl group.

4. A thiazole compound according to claim 1 or 2, wherein $R_2$ is a methyl group or a methoxymethylene group.

5. A thiazole compound according to claim 1 or 2, wherein $R_3$ is a 2-sulfoxybenzoylamino group.

6. A thiazole compound according to claim 1, which is

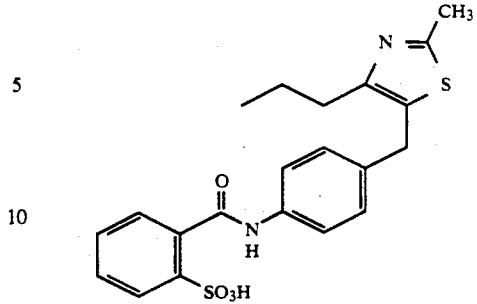

or

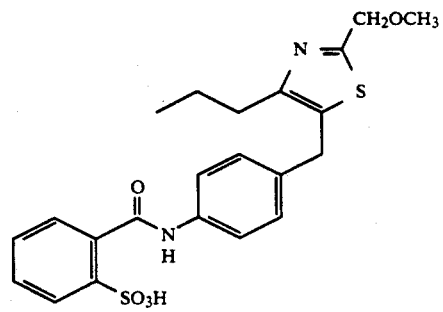

7. A pharmaceutical composition for the treatment of arterial hypertension and cardiac insufficiency which comprises an effective amount of at least one compound according to claim 1 or 2 in combination with a pharmaceutically acceptable carrier.

8. A method for treating arterial hypertension and cardiac insufficiency in an mammal in need of such treatment which comprises administering to the mammal an effective amount of a compound according to claim 1 or 2.

* * * * *